(12) United States Patent
Wahren et al.

(10) Patent No.: US 7,214,659 B2
(45) Date of Patent: May 8, 2007

(54) REDUCTION OF THE ELECTROCARDIOGRAPHIC QT INTERVAL

(75) Inventors: John Wahren, Djursholm (SE); Bo-Lennart Johansson, Uttran (SE); Joseph Bianchine, Research Triangle Park, NC (US)

(73) Assignee: Creative Peptides Sweden AB, Djursholm (SE)

( * ) Notice: Subject to any disclaimer, the term of this patent is extended or adjusted under 35 U.S.C. 154(b) by 430 days.

(21) Appl. No.: 10/380,301

(22) PCT Filed: Sep. 12, 2001

(86) PCT No.: PCT/GB01/04095

§ 371 (c)(1),
(2), (4) Date: Aug. 7, 2003

(87) PCT Pub. No.: WO02/22211

PCT Pub. Date: Mar. 21, 2002

(65) Prior Publication Data

US 2004/0033937 A1    Feb. 19, 2004

(30) Foreign Application Priority Data

Sep. 12, 2000 (GB) ............................... 0022342.0

(51) Int. Cl.
*A61K 38/00* (2006.01)
(52) U.S. Cl. .............................................. 514/3; 514/2
(58) Field of Classification Search ..................... None
See application file for complete search history.

(56) References Cited

U.S. PATENT DOCUMENTS 6,610,649 B2 * 8/2003 Wahren et al. .................. 514/2

FOREIGN PATENT DOCUMENTS

| WO | WO 98/13384 A |   | 4/1998 |
|----|---------------|---|--------|
| WO | WO 9813384 A  | * | 4/1998 |
| WO | WO 02/36129 A |   | 5/2002 |

OTHER PUBLICATIONS

Sawicki et al., Diabetologia 1996, vol. 39, pp. 77-81.*
Ido et al., 1997, Science vol. 277, pp. 563-566.*
Sovik, et al., Diabetes Care, 1999, vol. 22, Suppl. 2, B40-42.*
Wahren, et al., "Role of C-Peptide In Human Physiology", *Am. J. Physiol. Endocrinol. Metab.*, 278(5):E759-E768 (2000).
Bellavere, et al., Diabetes, Abstract only, 41(5):633-640 (1992).
Cameron, et al. , *Diabetes*, Abstract only, 46(Suppl. 2):S31-S37 (1997).
Cotter, et al., *ADA Meeting in Philadelphia*, Abstract only, (2001).
Davey, P., *Eur. J. Heart Fail.*, Abstract only, 2(3):265-271 (2000).
Ewing, et al., *Diabetologia*, Abstract only, 34(3):182-185 (1991).
Ewing, et al., *Diabetic Med.*, Abstract only, 7(1):23-26 (1990).
Forst, et al., *Diabetes*, Abstract only, 48;A201 (1999).
Forst, et al., *J. Clin. Invest.*, 101(10):2036-2041 (1998).
Galetta, et al., *G. Ital. Cardiol.*, Abstract only, 29(6):675-678 (1999).
Gastaldelli, et al., *Am. J. Physiol. Regul. Integr. Comp. Physiol.*, Abstract only, 279(6):R2022-R2025 (2000).
Hansen, et al., *Supplementum 2 für Kardiologie*, Abstract only, Band 90, 1023 (2001).
Hansen, et al., *EASD Meeting in Glasgow*, Abstract only, (2001).
Jermendy, et al., *Acta Cardiol.*, Abstract only, 46(2):189-200 (1991).
Johansson, et al., *Diabetic Med.*, 17:1-9 (2000).
Johansson, et al., *Diabetologia*, 39:687-695 (1996).
Johansson, et al., *Diabetologia*, 35:1151-1158 (1992).
Johansson, et al., *J. Clin. Endocrinol. Metabol.*, 77(4):976-981 (1993).
Kahn, et al., *J. Clin. Endocrinol. Metab.*, Abstract only, 64(4):751-754 (1987).
Katsuoka, et al., *Clin. Auton. Res.*, Abstract only, 8(3):139-143 (1998).
Lengyel, et al., *Orv. Hetil.*, Abstract only, 138(6):337-341 (1997).
Lindström, et al., *Acta Physiol. Scand.*, 156:19-25 (1996).
Lo, et al., *Am. J. Cardiol.*, Abstract only, 72(3):305-309 (1993).
Maffi, et al., *Diabetes*, Abstract only, 48:A55 (1999).
Meyer, et al., *Transplantation*, 66(2):233-240 (1998).
Miyamoto, et al., *Jpn. J. Pharmacol.*, Abstract only, 86(1):114-119 (2001).
Ohtomo, et al., *Diabetologia*, 39:199-205 (1996).
Oka, et al., *Diabetes Res. Clin. Pract.*, Abstract only, 31(1-3):63-70 (1996).
Pitkänen, et al., *Diabetes*, 47:248-254 (1998).
Rigler, et al., *PNAS*, 96(23):13318-13323 (1999).
Rossing, et al., *Diabetic Med.*, Abstract only, 18(23):199-205 (2001).
Sagie, et al., *Am. J. Cardiol.*, Abstract only, 70(7):797-801 (1992).
Sawicki, et al., *Diabetologia*, 39(1):77-81 (1996).
Sivieri, et al., *Diabetic Med.*, Abstract only, 10(10):920-924 (1993).
Tattersall, et al. *Diabetic Med.*, 8:49-58 (1991).
Tentolouris, et al., *Eur. J. Clin. Invest.*, Abstract only, 27(12):1049-1054 (1997).
Veglio, et al., *Diabetic Med.*, Abstract only, 12(4):302-306 (1995).
Veglio, et al., *Diabetic Care*, Abstract only, 23(9):1381-1383 (2000).
Weston, et al., *Diabetic Medicine*, 16:626-631 (1999).
Weston, et al., *Heart*, Abstract only, 78(1):56-60 (1997).
Ahnve et al., "Prognostic importance of $QT_c$ interval at discharge after acute myocardial infarction: a multicenter study of 865 patients", *Am. Hear J.*, 108(2):395-400 (1984).

* cited by examiner

*Primary Examiner*—B. Dell Chism
(74) *Attorney, Agent, or Firm*—Mintz, Levin, Cohn, Ferris, Glovsky and Popeo, P.C.; Ingrid A. Beattie

(57) ABSTRACT

The present invention relates to the use of proinsulin C-peptide or a variant, derivative or fragment thereof in the manufacture of a medicament for reducing the OTc interval and the use of proinsulin C-peptide or a variant, derivative or fragment thereof in the manufacture of a medicament for reducing the risk of sudden death or 'dead in bed' syndrome; particularly in patients suffering from IDDM.

10 Claims, 6 Drawing Sheets

REDUCTION OF THE ELECTROCARDIOGRAPHIC QT INTERVAL

The present invention relates to therapies whereby QT interval prolongation is normalised and the risk of sudden death or 'dead in bed' syndrome is reduced.

It has been observed (Davidson's Principles and Practice of Medicine, 17th Ed., p. 266) that a family history of sudden death in childhood or young adult life is sometimes associated with prolongation of the QT interval on the ECG (electrocardiogram). More specifically, several recent studies have shown that patients with insulin dependent diabetes mellitus (IDDM) have a higher prevalence of QT interval prolongation (Lengyel et al. Orv Hetil 1997; 138(6): 337–41). The QT interval reflects the time between the start of electrical activation of the myocardial ventricular wall and completion of its repolarization. QT duration is dependent on the heart rate, when corrected for heart rate influence, QT is denoted QTc. QTc is prolonged among patients with ischaemic heart disease (Ahnve et al., American Heart Journal 1984; 108: 395–400), diabetes mellitus (Sawicki et al., Diabetologia 1996; 39: 77–81) and after modulation of the autonomic nervous system with drugs (Tentolouris et al., Eur. J. Clin. Invest. 1997; 27(12): 1049–54). The pathogenesis of QTc prolongation is not known and no medication for or treatment of prolonged QTc is currently available.

QTc prolongation, known to be associated with arrhythmias, may have a role in the 'dead in bed' syndrome of insulin-dependent diabetes mellitus (IDDM) patients, in which seemingly healthy diabetic patients die unexpectedly without immediate cause. A preliminary study (Tattersall et al., Diabet. Med. 1991; 8: 49–58) reported a series of 22 unexplained deaths in patients with IDDM, all of whom were less than 50 years old. The deaths followed a well defined pattern, they occurred at night and the patients were found the next morning in an undisturbed bed. They had been seen the day before in good health and the autopsy consistently revealed no anatomical cause for death. Only a small minority of patients had documented ante-mortem evidence of diabetic complications, and in only one patient was there definite evidence of autonomic neuropathy. The phenomen became known as the 'dead in bed syndrome'. Since 1991 more than 80 young diabetic patients have died in sudden death syndrome in Scandinavia alone (Weston et al., Diabet. Med. 1999; 16(8): 626–31). It is therefore important to establish the cause and even more important to find a cure. QTc prolongation might be decreased with angiotensin-converting enzyme inhibitors or β-blockers, but QTc prolongation is not a recognised indication for administration of these drugs which have significant adverse effects.

The present invention is based on the surprising observation that proinsulin C-peptide is able to reduce the QTc interval in patients exhibiting QTc interval prolongation. Given the documented correlation between QTc interval prolongation and 'dead in bed' syndrome, this observation suggests a novel prophylactic treatment of 'dead in bed' syndrome. In particular the QTc interval can be reduced in patients with IDDM.

C-peptide has long been thought not to have any biological activity. It is synthesised in the beta cells of the pancreas and released into the circulation in equimolar amounts together with insulin. The C-peptide amino acid chain is a part of the proinsulin molecule and it is thought to assist in achieving the correct folding structure. When the proteolytic process starts the proinsulin is cleaved into insulin and C-peptide. Human C-peptide is a 31 amino acid peptide having the following sequence: EAEDLQVGQVELGGGP-GAGSLQPLALEGSLQ (SEQ ID NO:1).

C-peptide binds to the cell surface and stimulates $Na^+K^+$-ATPase and endothelial nitric oxide synthase (eNOS) activity, probably via a G-protein coupled reaction followed by activation of $Ca^{2+}$-dependent intracellular signaling pathways. Studies have shown that administration of C-peptide can decrease glomerular hyperfiltration, improve blood-retinal barrier function (Johansson et al., J. Clin. Endocrinol. & Metab. 1993; 77: 976–981) and ameliorate autonomic and sensory nerve function in patients with IDDM (Johansson et al., Diabetologia 1996; 39: 687–695). Active fragments of C-peptide have been described for treating diabetic neuropathy, nephropathy and retinopathy (WO98/13384 but not for improving myocardial complications of diabetes such as an elongated QTc interval. A proportion, perhaps 2–10%, of patients with IDDM will exhibit an elongated QTc interval but this group will not necessarily also exhibit diabetic neuropathy/nephropathy etc., there being no known association between the conditions.

Thus, in one aspect the present invention provides the use of proinsulin C-peptide in the manufacture of a medicament for reducing the QTc interval, typically in patients exhibiting QTc interval prolongation. Generally the patients will have IDDM. However, QTc interval prolongation is also observed in other patients such as those with ischaemic heart disease and those who have received drugs which modulate the autonomic nervous system and such patients may also benefit from the treatments discussed herein.

Alternatively viewed, the invention provides proinsulin C-peptide for use in reducing the QTc interval, typically in patients exhibiting QTc interval prolongation, generally in patients with IDDM.

In a further aspect, the present invention provides the use of proinsulin C-peptide in the manufacture of a medicament for the prophylactic treatment (i.e. prevention, including reducing the risk) of sudden death or 'dead in bed' syndrome. This syndrome is discussed above and patients who are believed to be at risk of 'dead in bed' syndrome will typically be those exhibiting QTc interval prolongation, generally patients with IDDM.

Alternatively viewed the invention provides proinsulin C-peptide for use in the prophylactic treatment of sudden death or 'dead in bed' syndrome.

According to a further aspect, the present invention provides a method of reducing the QTc interval in a mammal, which method comprises administering proinsulin C-peptide to said mammal in an amount effective to reduce said QTc interval.

In a yet further aspect, the present invention provides a method of preventing or reducing the risk of sudden death or 'dead in bed' syndrome in a human or animal patient who is at risk thereof, which method comprises administering proinsulin C-peptide in an amount effect to reduce the QTc interval in said patient. Patients at risk of 'dead in bed' syndrome can be identified as those exhibiting QTc interval prolongation and will typically be sufferers of IDDM.

The invention relates to human proinsulin C-peptide itself as well as functionally equivalent variants, derivatives or fragments thereof. Such variants may include, for example, different allelic variants as they appear in nature, e.g. in other species or due to geographical variation etc. Functionally equivalent derivatives include peptides which incorporate amino acid substitutions, or intra-sequence or terminal deletions or additions to the above sequence, and also chemical modifications thereof, including for example the inclusion of chemically substituted or modified amino acid residues, provided they retain the ability to reduce the QTc interval.

The variants, derivatives and fragments are functionally equivalent in that they exhibit at least 40%, preferably at least 60% of the activity of human proinsulin C-peptide. Activity being measured in terms of an ability to reduce the QTc interval as described herein.

Also included within the scope of the invention is the use of "non-native" isomers of "native" L-amino acid C-peptide sequences, e.g. peptides containing D-amino acid isomers.

It is known in the art to modify the sequences of proteins or peptides, whilst retaining their useful activity, and this may be achieved using techniques which are standard in the art and widely described in the literature e.g. random or site-directed mutagenesis, cleavage and ligation of nucleic acids, chemical peptide synthesis etc.

A peptide may conveniently be chosen which is human proinsulin C-peptide or a functional fragment thereof or a functional peptide which has an amino acid sequence which is 70%, preferably 80%, more preferably 90% identical to C-peptide or a fragment thereof.

As far as fragments are concerned, these include both fragments of the native human proinsulin C-peptide sequence as set out above, or fragments of any functionally equivalent variant or derivative as mentioned above, provided that the fragment retains the biological or therapeutically beneficial activity of the "whole" or "complete" molecule. Preferred fragments comprise residues 15–31 of native C-peptide, more especially residues 20–31. Peptides comprising the pentapeptide EGSLQ (residues 27–31 of native human C-peptide) are particularly preferred. The fragment may thus vary in size from e.g. 2 to 30 amino acids, preferably 3 to 20, e.g. 3 to 12, or 4 to 10 residues. The fragments will typically have at least 5 amino acid residues, e.g. 5 to 12 residues.

Representative fragments include or comprise in particular peptide A (ELGGGPGAG) (SEQ ID NO:2) or peptide E (EGSLQ) (SEQ ID NO:3) mentioned in W098/13384 of Creative Peptides Sweden AB, sub-fragments of peptides A and E may also be used and these are described in more detail in WO 98/13384. Exemplary mention may be made of peptide B (ELGG) (SEQ ID NO:4), peptide C (ELGGGP) (SEQ ID NO:5), peptide D (GGPGA) (SEQ ID NO:6) and peptide F (GSLQ) (SEQ ID NO:7). Also included with the scope of definition of "proinsulin-C peptide" according to the present invention are peptides having N- and/or C-terminal extensions; or flanking sequences, to the sequences of proinsulin C-peptide or a fragment, thereof. Such flanking or extension sequences may be non-native. The length of each "extended" derivative may vary, but preferably the peptides are not more than 50, e.g. not more than 30, or 25 or 20, especially not more than 15 or 10 amino acids in length. For example, the peptides maybe 3 to 50, 3 to 30, 3 to 25, 3 to 20, 3 to 15 or 3 to 10 amino acids in length.

Accordingly, by "proinsulin C-peptide" is meant native, isolated proinsulin C-peptide whether modified or unmodified, as well as synthesised peptides, and all such variants, derivatives and fragments as are described above.

In addition, the term "proinsulin C-peptide" encompasses non-peptide compounds showing the same effects as displayed by their C-peptide-derived counterparts. Such peptidomimetics or "small-molecules" capable of mimicking the activity of the naturally occurring proteins or peptides are likely to be better suited for e.g. oral delivery due to their increased chemical stability.

It is now commonplace in the art to replace peptide or protein-based active agents e.g. therapeutic peptides, with such peptidomimetics having functionally-equivalent activity. Various molecular libraries and combinatorial chemistry techniques exist and are available to facilitate the identification, selection and/or synthesis of such compounds using standard techniques (Kieber-Emons, T. et al., Current Opinion in Biotech. 1997; 8: 435–441). Such standard techniques may be used to obtain the peptidomimetic compounds for use according to the present invention, namely peptidomimetic organic compounds which show the same or substantially similar or even better reduction of the QTc interval, e.g. as is shown by the peptides described herein in the Examples.

The suitability of a given proinsulin C-peptide for use according to the invention can be determined by its ability to reduce the QTc interval according to the protocol described in the Examples herein.

The QTc interval will vary from patient to patient but can generally be considered prolonged when it exceeds 420 ms in men and 430 ms in women. QTc is the corrected (for heart rate influence) QT interval. It is calculated according to Bazett's formula ($QTc=QT/\sqrt{RR}$). QT and RR are conveniently measured using a ruler on an ECG tracing; the QT interval is measured from the beginning of the QRS complex to the end of the crossing of the isoelectric line of the T wave, see the stylised representation in FIG. 1. The RR interval is measured from one R peak to the next, again as shown in FIG. 1. Any reduction in the interval can be beneficial to the patient, preferably the interval will be reduced by at least 3 ms, more preferably treatment will reduce the QTc interval by at least 5 ms, particularly preferably at least 8 ms even at least 10 ms.

In addition, many drugs administered to diabetic patients increase the QTc interval so even a modest decrease may be clinically important.

Patients with IDDM generally have very low circulating levels of proinsulin C-peptide and the therapies of the present invention preferably result in a normalisation of circulating proinsulin C-peptide levels. Preferably the patient will have 60 to 140, e.g. 80–120% of the normal physiological level of circulating proinsulin C-peptide as a result of the administration in accordance with the present invention.

Compositions comprising proinsulin C-peptide as defined above are preferably formulated prior to administration.

The present invention therefore also provides a pharmaceutical composition for use in the reduction of the QTc interval and/or the prevention of 'dead in bed' syndrome (sudden death), said composition comprising proinsulin C-peptide together with at least one pharmaceutically acceptable carrier, diluent or excipient.

The active ingredient in such compositions may comprise from 0.05% to 99% by weight of the formulation, more preferably 0.1% to 1.0%.

By "pharmaceutically acceptable" is meant that the ingredients must be compatible with other ingredients of the composition as well as physiologically acceptable to the recipient.

Pharmaceutical compositions for use in methods according to the present invention may be formulated according to techniques and procedures well known in the art and widely described in the literature, and may comprise any of the known carriers, diluents or excipients. Other ingredient may of course also be included, according to techniques well known in the art e.g. stabilisers, preservatives, etc. The formulations may be in the form of sterile aqueous solutions and or suspensions of the pharmaceutically active ingredients, aerosols, ointments and the like.

A preferred embodiment of the present invention are sustained release forms of proinsulin C-peptide which are well known in the art, e.g. microparticles, nanoparticles, emulsions, nanosuspensions, lipid particles or oils. Especially preferred are sustained release forms based on microparticles.

Materials used for the production of said microparticles are well known in the art and comprise e.g. mono- or copolymers based on lactite, glycolite, vinyl acetate, dextrans, dextransulfates, hydroxybutyrate, valerolacton, caprolacton, acrylic acid or methacrylic acids. Especially preferred are microparticles based on polylactite or polyglycolite. Examples for the production of such particles are given in patent application No. WO 94/09898.

Another preferred embodiment of the present invention are films, patches or folios having proinsulin C-peptide coated on the surface, incorporated in a special layer or incorporated in the matrix composition. An especially preferred embodiment are biodegradable folios having proinsulin C-peptide coated on the surface or incorporated in the composition. Preferred materials of said preferred biodegradable folios are polymers or copolymers of lactite and glycolite.

The administration may be by any suitable method known in the medicinal arts, including oral, parenteral, topical, subcutaneous administration or by inhalation.

The peptides may be administered in a single dose to be taken at regular intervals, or as divided doses to be taken/administered e.g. 1 to 6 times during the course of a day. Sustained release formulations are preferably given at longer intervals, e.g. 1 to 2 times a month or every three months.

The precise dosage of the active compounds to be administered, the number of daily or monthly doses and the length of the course of treatment will depend on a number of factors, including the age of the patient and the degree of QTc interval prolongation.

Conveniently, the C-peptide may be administered intravenously or sub-cutaneously. Typical doses will range from 300–1000 nM per day, e.g. 500–800 rM per day, this total dose preferably being split between 2 or more doses during the 24 hour period, typically being split between 3 or 4 doses. Patients who would benefit from the treatments proposed herein will often be those who take several daily doses of insulin (e.g. by sub-cutaneous self injection) and administration of C-peptide can follow a similar pattern. Insulin and C-peptide may therefore effectively be administered at the same or substantially the same time, but preferably not in a mixed formulation. As the C-peptide may be administered by injection, the 'medicament' comprising it will typically be in liquid form comprising one or more solvents as well as the active ingredient(s). The treatment program will follow the typical pattern of chronic treatment and is likely to last for months, possibly for the life of the patient.

The compositions may be formulated according to techniques and procedures well known in the literature, and may comprise any of the known carriers, diluents or excipients. Thus, for example, compositions for use in the methods of this invention which are suitable for parenteral administration conveniently comprise sterile aqueous solutions and/or suspensions of pharmaceutically active ingredients preferably made isotonic with the blood of the recipient, generally using sodium chloride, glycerin, glucose, mannitol, sorbitol and the like. In addition the composition may contain any of a number of adjuvants, such as buffers, preservatives, dispersing agents, agents that promote rapid onset of action or polonged duration of action and the like.

Compositions suitable for oral administration may, for example, comprise active fragments/peptides of the proinsulin C-peptide molecule or the whole molecule in sterile purified stock powder form, preferably covered by an envelope or envelopes (enterocapsulae) protecting the active peptides from degradation (decarboxylation or hydrolysis) in the stomach and thereby enabling absorption of these substances from the gingiva or in the small intestine. The envelope(s) may contain any of a number of adjuvants such as buffers, preservative agents, agents that promote prolonged or rapid release giving an optimal bioavailability of the compositions. Furthermore, compositions for use in the methods of this invention suitable for local or topical administration may comprise active fragments of the proinsulin C-peptide molecule or the whole molecule in sterile formulation mixed with known suitable ingredients, such as paraffin, vaseline, cetanol, glycerol and its like, to form suitable ointments or creams.

The invention will now be described in more detail in the following non-limiting Examples which show, with reference to the following drawings.

Figure 4:
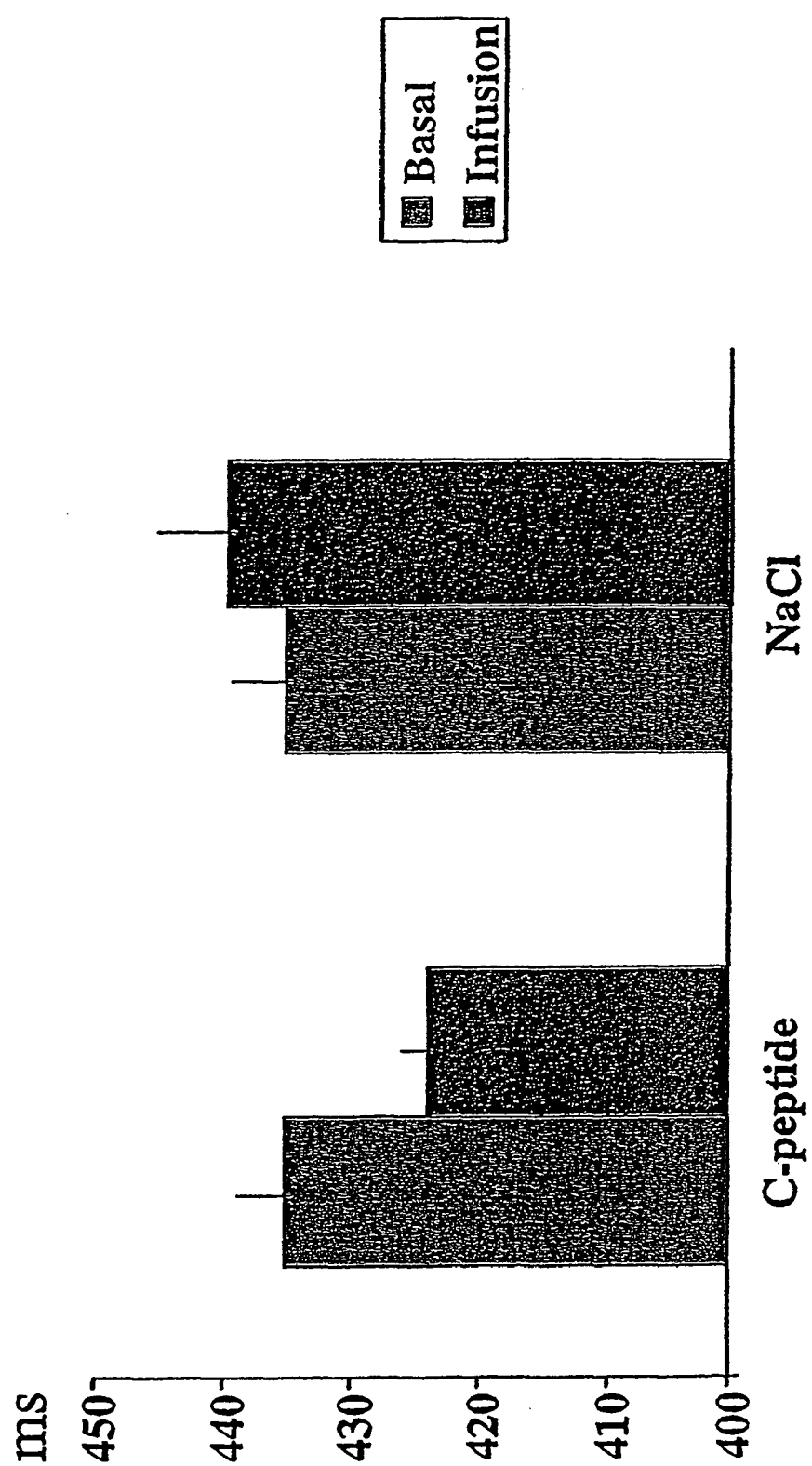

FIG. 4 is a graph showing the influence of proinsulin C-peptide on QTc interval in 13 patients with IDDM, after 3 hours infusion as described in Example 3. The 13 patients are made up of the 8 patients of Example 1 plus the 5 (from 12) patients of Example 3 who exhibit QTc prolongation.

Figure 5:
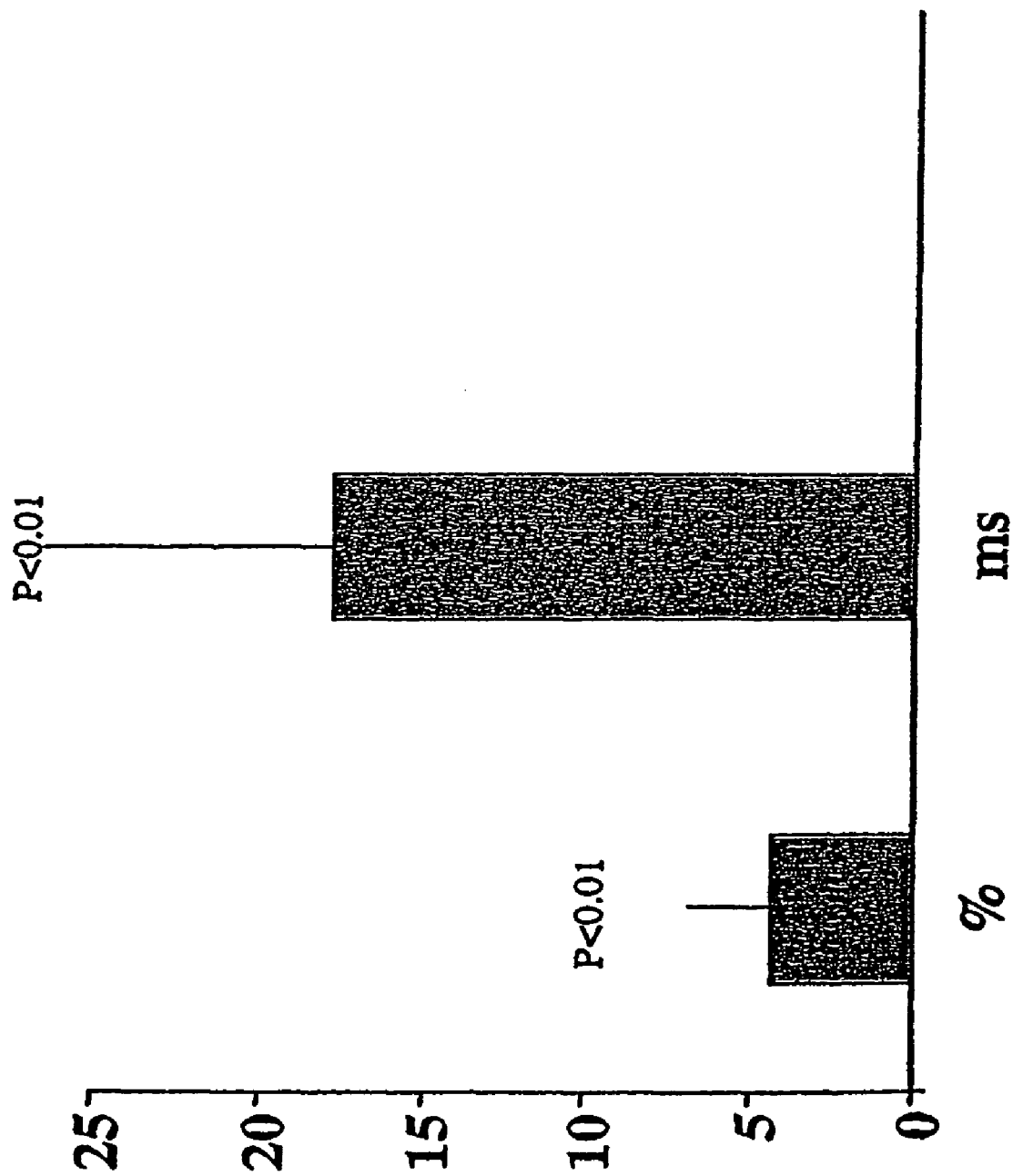

FIG. 5 is a graph showing the differences in QTc interval between the C-peptide and placebo (NaCl) infusion periods in percentage (%) and in real terms (ms) for the 13 patients of FIG. 4 described above plus the 6 patients of Example 2.

Figure 6:
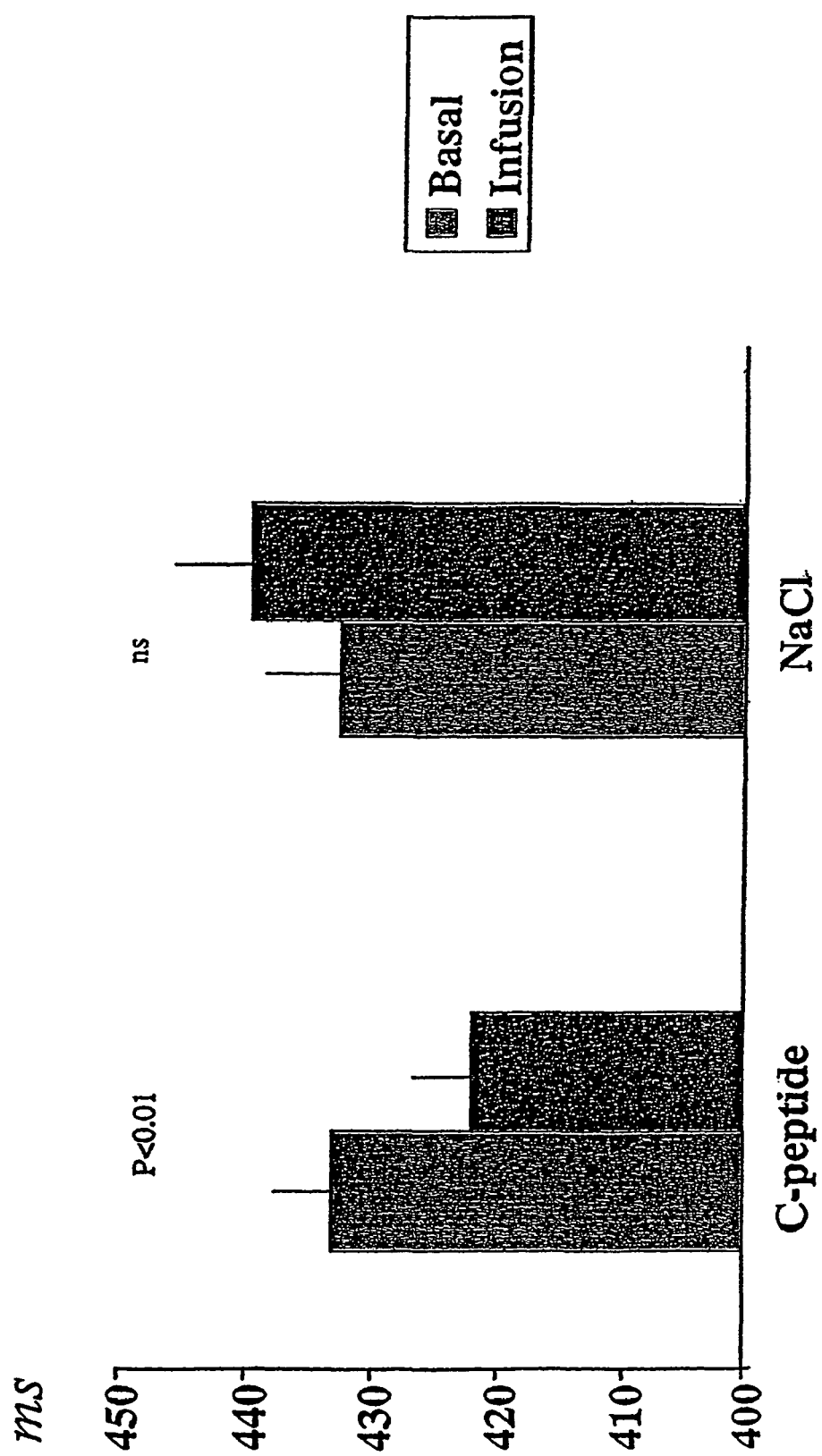

FIG. 6 is a graph showing the influence of proinsulin C-peptide and placebo on the QTc interval of the patients with prolonged basal QTc. This group of 19 patients is the same as described above in respect of FIG. 5.

EXAMPLE 1

Electrocardiograms from a study by Johansson et al. carried out in 1996 (other aspects of this study were reported in Johansson et al., 1996, supra) were examined and this paper is incorporated herein by reference.

In this study 12 IDDM patients (six male and six female) with autonomic neuropathy participated in two different sessions in a randomized, double-blind study (one patient attended one time only). Their mean age was 40 and mean duration of diabetes was 21 years. In eight patients the fasting plasma C-peptide levels were below the detection limit (<0.10 nmol/l), the remaining four varied between 0.13 and 0.25 nmol/l. Eleven patients had decreased heart rate variability during deep breathing as evidence of autonomic neuropathy. On each occasion they received insulin i.v. for 9–12 hours before the study and blood glucose levels were tested every 1–2 hours during the night. The insulin infusion was adjusted to achieve euglycaemia (5–6 mmol/l). The patients were then given either saline or C-peptide i.v. for 180 minutes. 6 pico mole per kg per minute was administered.

Before and during the three hour session a complete 12 lead electrocardiogram was recorded to evaluate heart rate variability during deep breathing. These recordings were then used to measure the corrected QT interval (QTc) according to the Bazett's formula (QTc=QT/√RR). The 44 ECG tracings (one patient could not take part in a second session and one patient's ECG tracing was not possible to evaluate) were analyzed blindly by two persons. The RR and QT interval were measured with a ruler. The QT interval was taken from the beginning of the QRS complex to the crossing of the isoelectric line of the T wave. Five intervals from the precordial leads and five intervals from the extremity leads were measured on each occasion and a mean was calculated. The two observers compared their QTc values if there was a difference greater than 5%, it was recalculated. P values less than 0.05 were considered statistically significant.

Figure 1:
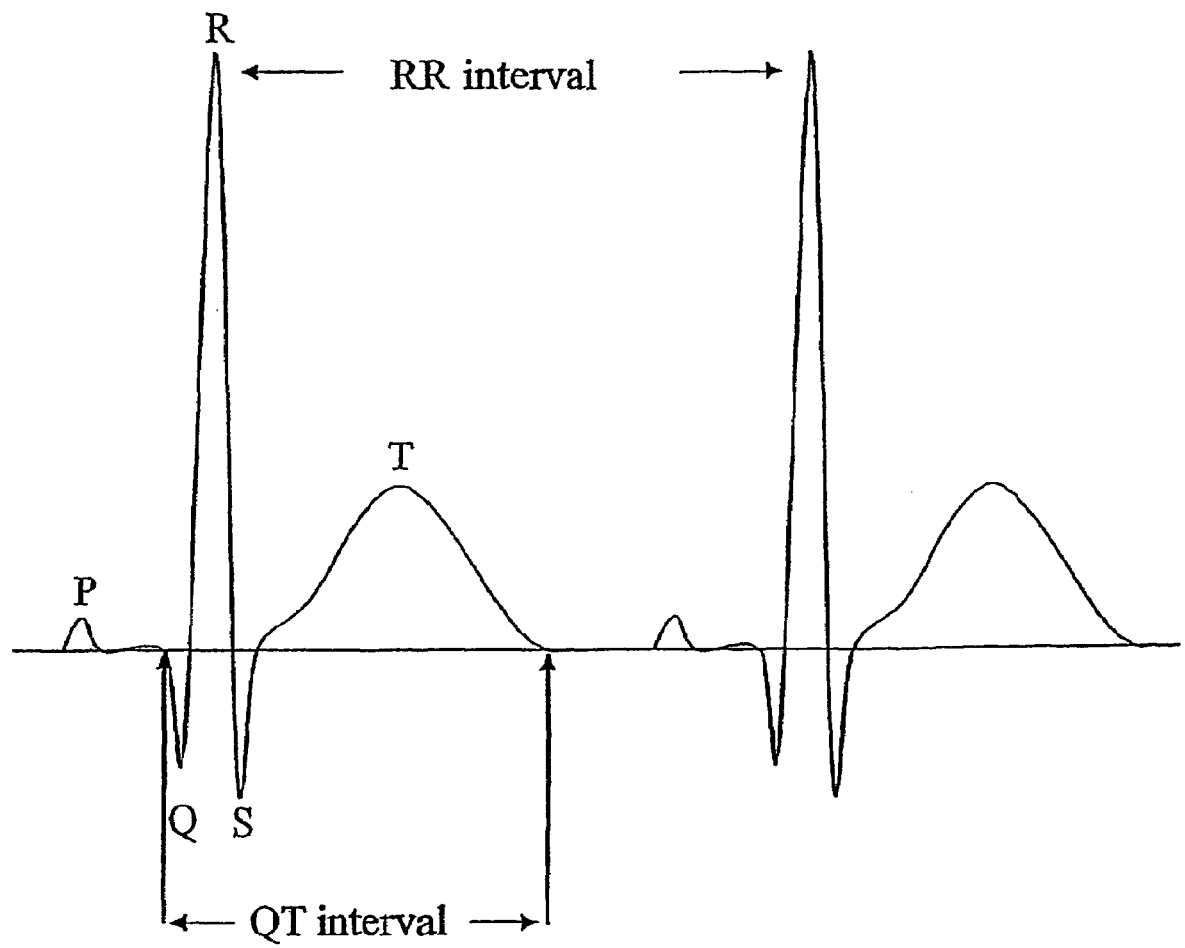
FIG. 1 is a schematic representation of a typical ECG trace showing the QT and RR intervals. The P wave represents atrial activation, the QRS complex ventricular activation and the T wave ventricular recovery.
Figure 2:
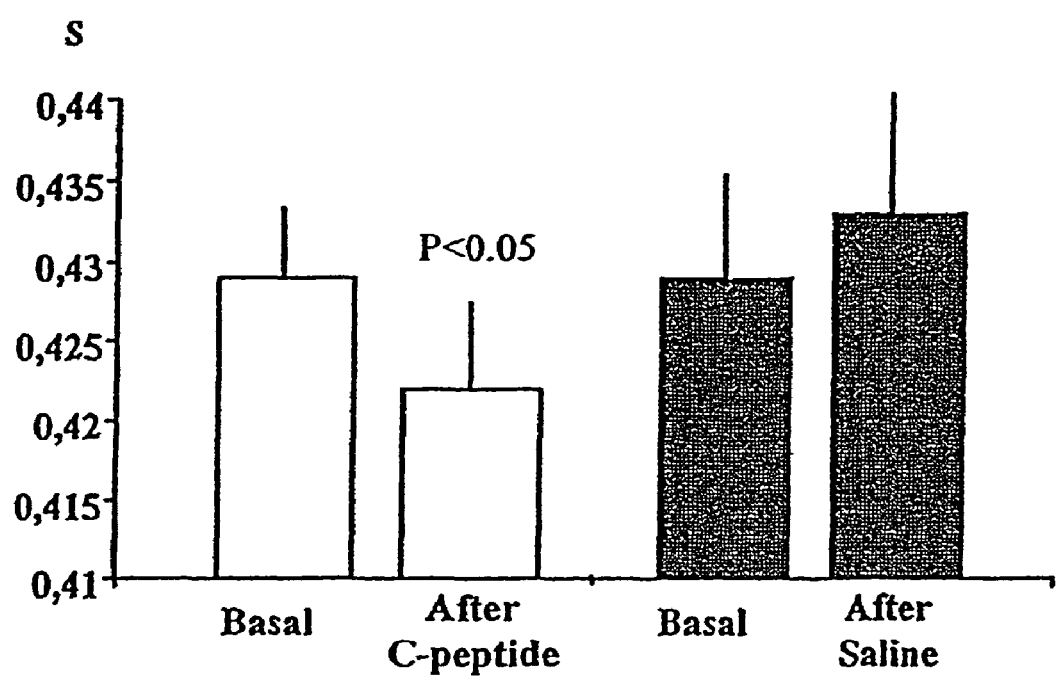
FIG. 2 is a graph showing the influence of proinsulin C-peptide on QTc intervals in seconds according to the study described in Example 1 herein.

Mean C-peptide levels rose from 0.11±0.02 nmol/l before the study to 1.73±0.04 nmol/l during the C-peptide infusion (within normal physiological range), whereas the C-peptide plasma concentration remained below detection limit (0.10 nmol/l) during saline infusion. Blood glucose levels decreased slightly during C-peptide infusion (from 6.3 to 5.9 mmol/l) and during the saline infusion it was almost unchanged. There was no difference in the basal QTc interval on the two study occasions (0.429±0.004s). During the three hours of C-peptide administration the mean QTc interval decreased significantly (0.422±0.006; p<0.05), whereas the QTc interval rose slightly during the saline infusion (n.s.) (FIG. 2). This study demonstrates that infusion of C-peptide significantly decreases the QTc interval. Although the reduction is small in percentage terms the drop is significant in physiological and clinical terms.

EXAMPLE 2

In a further study (different results from which were published in Diabetic Medicine, Vol. 17 (2000) p. 181–189, Johannson, Bo-Lennart et al.) 21 IDDM patients were monitored for 6 months according to a randomised cross over regimen wherein C-peptide was administered for 3 months and a placebo.

Further details of the study can be found in the above referenced paper in Diabetic Medicine but in summary, biosynthetic human C-peptide (Eli Lilly Co.) or a placebo comprising just the C-peptide solvent was injected subcutaneously 3 times per day. The total 24 h dose of C-peptide was 600 nmol (225 nmol 30 mins before breakfast, 150 nmol before dinner and 225 nmol at bedtime).

ECGs were recorded at the start of the programme and after 3 and then 6 months of the study. These recordings were then used to measure the QTc interval as described in Example 1.

Figure 3:
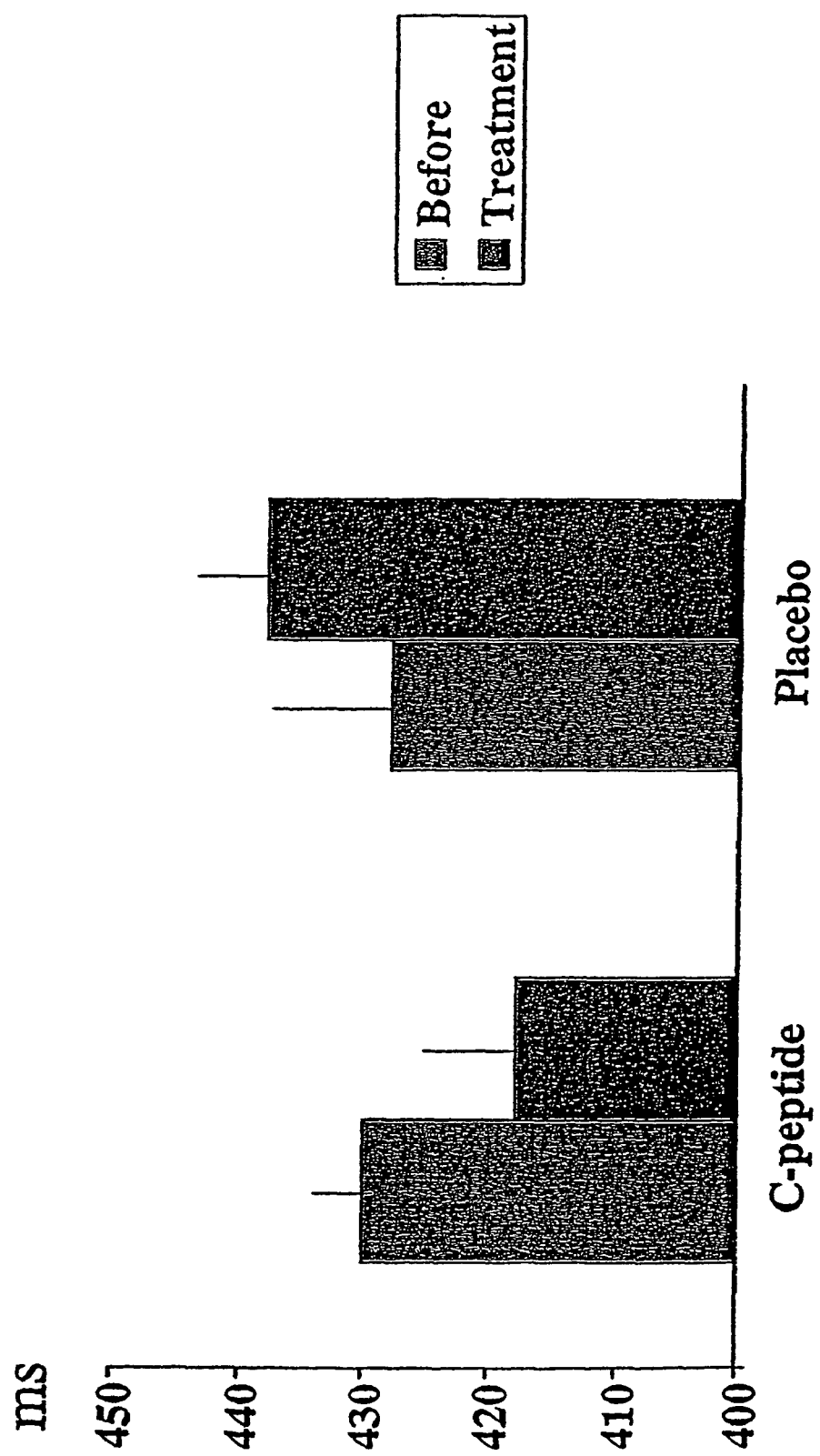
FIG. 3 is a graph showing the influence of proinsulin C-peptide on QTc interval in 6 patients with IDDM, after 3 months of treatment as described in Example 2.

Those patients (6) who exhibited a prolonged QTc interval at the outset (>420 ms) showed a clear shortening of the QTc interval during the C-peptide phase as compared to the placebo phase (FIG. 3).

EXAMPLE 3

In a further study, it has been shown that a short period of C-peptide administration may still be sufficient to reduce the QTc interval.

Twelve patients were investigated twice in a randomised double blind study where C-peptide or a NaCl placebo were infused for 3 hours. The same procedure as described in Example 1 was followed.

The ECGs were analysed as described in the previous examples and a decrease in QTc interval during C-peptide treatment as compared to during administration of a placebo was observed as shown in FIG. 4.

The differences in QTc interval between the C-peptide and NaCl infusion periods in percentage and in real time (ms) are shown in FIG. 5.

The invention claimed is:

1. A method of reducing the QTc interval, which method comprises identifying a human patient exhibiting a prolonged QTc interval and administering between 100–300 nM of proinsulin C-peptide or a fragment of human C-peptide comprising residues 15–31, 20–31 or 27–31 of SEQ ID NO:1 to said human patient to reduce said QTc interval.

2. A method of reducing the risk of sudden death or 'dead in bed' syndrome in a human patient who is at risk thereof, which method comprises identifying a human patient exhibiting a prolonged QTc interval and administering between 100–300 nM of proinsulin C-peptide or a fragment of human C-peptide comprising residues 15–31, 20–31 or 27–31 or SEQ ID NO:1 in an amount effect to reduce the QTc interval in said patient.

3. The method according to claims 1 or 2, wherein the fragment has a size of from 5 to 20 amino acid residues or 5 to 30 amino acid residues.

4. The method according to claims 1 or 2, wherein the proinsulin C-peptide or fragment of human C-peptide comprising residues 15–31, 20–31 or 27–31 of SEQ ID NO:1 is administered to a patient exhibiting QTc interval prolongation.

5. The method according to claims 1 or 2, wherein the proinsulin C-peptide or fragment of human C-peptide comprising residues 15–31, 20–31 or 27–31 of SEQ ID NO:1 is administered to a patient with insulin-dependent diabetes mellitus or ischaemic heart disease.

6. A method of reducing the QTc interval, which method comprises identifying a human patient exhibiting a prolonged QTc interval and administering a daily dose of 500–700 nM of proinsulin C-peptide or a fragment of human C-peptide comprising residues 15–31, 20–31 or 27–31 of SEQ ID NO:1 to said human patient to reduce said QTc interval.

7. A method of reducing the risk of sudden death or 'dead in bed' syndrome in a human patient who is at risk thereof, which method comprises identifying a human patient exhibiting a prolonged QTc interval and administering a daily dose of 500–700 nM of proinsulin C-peptide or a fragment of human C-peptide comprising residues 15–31, 20–31 or 27–31 of SEQ ID NO:1 to said human patient to reduce the QTc in said patient.

8. The method according to claims 6 or 7, wherein the fragment has a size of from 5 to 20 amino acid residues or 5 to 30 amino acid residues.

9. The method according to claims 6 or 7, wherein the proinsulin C-peptide or fragment of human C-peptide comprising residues 15–31, 20–31 or 27–31 of SEQ ID NO:1 is administered to a patient exhibiting QTc interval prolongation.

10. The method according to claims 6 or 7, wherein the proinsulin C-peptide or fragment of human C-peptide comprising residues 15–31, 20–31 or 27–31 of SEQ ID NO:1 is administered to a patient with insulin-dependent diabetes mellitus or ischaemic heart disease.

* * * * *

SEQUENCE LISTING

```
<160> NUMBER OF SEQ ID NOS: 7

<210> SEQ ID NO 1
<211> LENGTH: 31
<212> TYPE: PRT
<213> ORGANISM: Homo sapiens

<400> SEQUENCE: 1

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln
            20                  25                  30

<210> SEQ ID NO 2
<211> LENGTH: 9
<212> TYPE: PRT
<213> ORGANISM: Homo sapiens

<400> SEQUENCE: 2

Glu Leu Gly Gly Gly Pro Gly Ala Gly
1               5

<210> SEQ ID NO 3
```

-continued

```
<211> LENGTH: 5
<212> TYPE: PRT
<213> ORGANISM: Homo sapiens

<400> SEQUENCE: 3

Glu Gly Ser Leu Gln
1               5

<210> SEQ ID NO 4
<211> LENGTH: 4
<212> TYPE: PRT
<213> ORGANISM: Homo sapiens

<400> SEQUENCE: 4

Glu Leu Gly Gly
1

<210> SEQ ID NO 5
<211> LENGTH: 6
<212> TYPE: PRT
<213> ORGANISM: Homo sapiens

<400> SEQUENCE: 5

Glu Leu Gly Gly Gly Pro
1               5

<210> SEQ ID NO 6
<211> LENGTH: 5
<212> TYPE: PRT
<213> ORGANISM: Homo sapiens

<400> SEQUENCE: 6

Gly Gly Pro Gly Ala
1               5

<210> SEQ ID NO 7
<211> LENGTH: 4
<212> TYPE: PRT
<213> ORGANISM: Homo sapiens

<400> SEQUENCE: 7

Gly Ser Leu Gln
1
```